United States Patent [19]

Ishizumi et al.

[11] 4,067,868

[45] Jan. 10, 1978

[54] PRODUCTION OF QUINAZOLINONE COMPOUNDS

[75] Inventors: Kikuo Ishizumi, Ikeda; Kazuo Mori, Kobe; Michihiro Yamamoto, Nishinomiya; Masao Koshiba; Shigeho Inaba, both of Takarazuka; Hisao Yamamoto, Nishinomiya, all of Japan

[73] Assignee: Sumitomo Chemical Company, Limited, Osaka, Japan

[21] Appl. No.: 670,952

[22] Filed: Mar. 26, 1976

Related U.S. Application Data

[62] Division of Ser. No. 352,016, April 17, 1973, abandoned.

[51] Int. Cl.² ............................................. C07D 239/82
[52] U.S. Cl. .................... 260/251 QB; 260/326.13 R; 260/326.16; 548/307; 560/21; 560/27
[58] Field of Search ..................................... 260/251 Q

[56]  References Cited

U.S. PATENT DOCUMENTS

| 3,562,272 | 2/1971 | Ott ........................................ 260/251 |
| 3,686,178 | 8/1972 | Cooke et al. ................... 260/251 QB |
| 3,712,892 | 1/1973 | Inaba et al. .................... 260/251 QB |
| 3,876,665 | 4/1975 | Cooke et al. ..................... 260/340.5 |
| 3,925,382 | 12/1975 | Ishizumi et al. ............. 260/251 QB |
| 3,953,446 | 4/1976 | Ishizumi et al. ............. 260/251 QB |

FOREIGN PATENT DOCUMENTS 2,124   6/1972   Netherlands.

Primary Examiner—Raymond V. Rush
Attorney, Agent, or Firm—Stevens, Davis, Miller & Mosher

[57]  ABSTRACT

2(1H)-Quinazolinone derivatives, which are useful as anti-inflammatory agents, are prepared by heating or hydrolyzing an acylurea derivative. The acylurea derivative can be prepared by either reacting an indole derivative with an oxidizing agent or reacting an imidazolidine derivative with water, an alkanol or ammonia.

4 Claims, No Drawings

PRODUCTION OF QUINAZOLINONE COMPOUNDS

This is a division of application Ser. No. 352,016, filed Apr. 17, 1973, and now abandoned.

This invention relates to a process for preparing quinazolinone derivatives and intermediates thereof.

More particularly, this invention relates to a process for preparing quinazolinone derivatives of the formula,

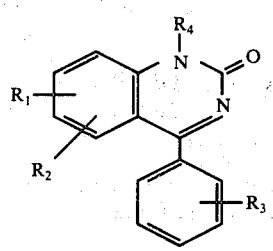

(I)

wherein $R_1$, $R_2$ and $R_3$ are independently a hydrogen atom, a halogen atom, a trifluoromethyl group, a nitro group, a lower alkyl group, or a lower alkoxy group; and $R_4$ is a hydrogen atom, a lower alkyl group, a polyhaloalkyl group, or a cycloalkylalkyl group, and intermediates thereof.

The term "halogen" includes all halogen atoms, i.e. fluorine, chlorine, bromine and iodine; the term "alkyl" means both straight and branched chain aliphatic hydrocarbon radicals, and lower alkyl is, for example, $C_1$-$_4$ alkyl which includes such groups as methyl, ethyl, n-propyl, isopropyl, n-butyl, iso-butyl, and tertiary-butyl; the term "lower alkoxy" is, for example, $C_{1-4}$ alkoxy which includes such groups as methoxy, ethoxy, n-propoxy, isopropoxy, n-butoxy and tertiary-butoxy; the term "polyhaloalkyl" is, for example, a trichloromethyl, trifluoromethyl, trichloroethyl, trifluoroethyl, or pentafluoropropyl group; the term "cycloalkylalkyl" is, for example, ($C_{3-6}$cycloalkyl)-$C_{1-4}$alkyl in which the $C_{3-6}$ cycloalkyl moiety includes such groups as cyclopropyl, cyclobutyl, cyclopentyl, cyclohexyl, methylcyclopropyl and dimethylcyclopropyl, and the $C_{1-4}$ alkyl moiety is as mentioned above.

It is known that the quinazolinone derivatives of the formula [I] can be prepared by reacting an o-aminobenzophenone derivative of the formula,

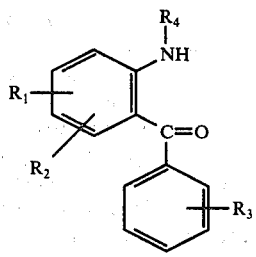

[II]

wherein $R_1$, $R_2$, $R_3$ and $R_4$ are as defined above, with, for example, an urea. But the above-mentioned process has many disadvantages as mentioned below; many of the starting o-aminobenzophenone derivatives of the formula [II] are difficult to obtain by synthesis; the compound of the formula [II] having a substituent group such as an alkyl group as $R_4$, in general, has to be prepared through three stage procedures from that having a hydrogen atom as $R_4$; the condensation reaction mentioned above must be carried out at higher temperatures and the aftertreatment required for such process is very difficult to operate, etc.

It is an object of this invention to provide a novel process for preparing a quinazolinone derivative of the formula [I] using an easily obtainable indole derivative, without using an o-aminobenzophenone derivative which has many disadvantages as mentioned above, as a starting material. It is a further object of the present invention to provide a novel process for preparing a quinazolinone derivative of the formula [I] under mild reaction conditions overcoming many disadvantages of the process using an o-aminobenzophenone derivative as a starting material. Further objects and advantages of the present invention will be apparent to one skilled in the art from the accompanying disclosure and discussion.

The process of the present invention can be shown by the following reaction schema:

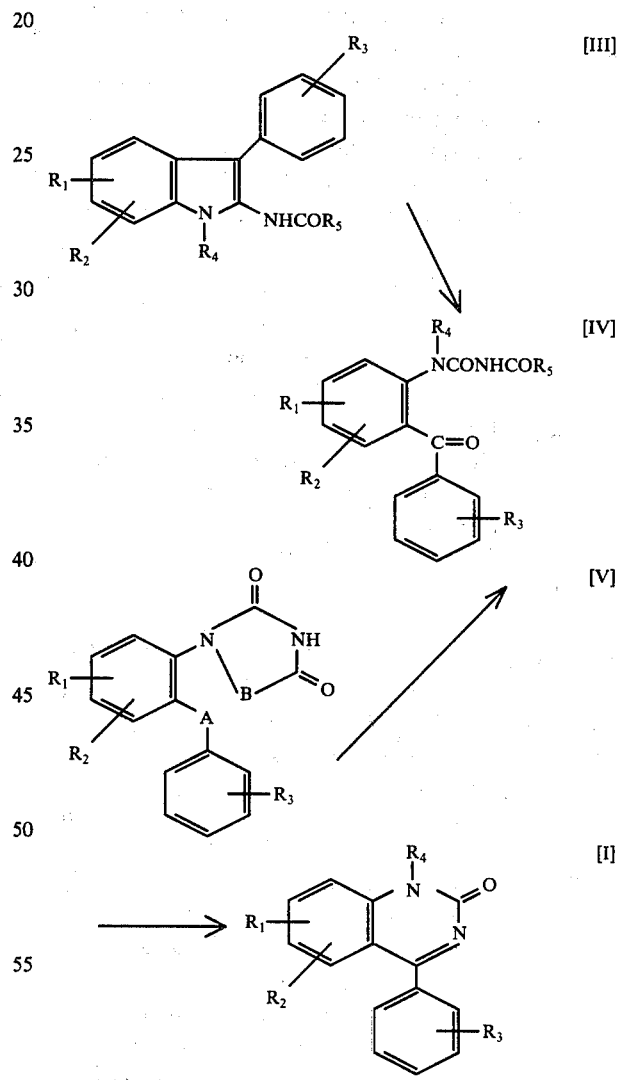

In the above formulae, $R_1$, $R_2$, $R_3$ and $R_4$ are as defined above; $R_5$ is a hydrogen atom, a lower alkyl group, a phenyl group, a lower alkoxy group, a benzyloxy group, an amino group, a carboxyl group, a carbamoyl group, or a lower alkoxycarbonyl group (provided that when an acylurea derivative of the formula [IV] is prepared from imidazolidine derivative of the formula [V], $R_4$ is a hydrogen atom and $R_5$ is a lower alkoxy group, an amino group, a carboxyl group, a carbamoyl group or a lower alkoxycarbonyl group in the formula [IV]); A and B are independently a C = O group or A together with B forms a group of the formula,

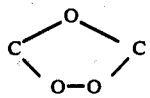

According to the process of the present invention, a quinazolinone derivative of the formula [I] is preparred by hydrolyzing or heating an acylurea derivative of the formula [IV].

The acylurea derivative of the formula [IV] can be prepared by a. reacting an indole derivative of the formula [III] with an oxidizing agent, or b. reacting an imidazolidine derivative of the formula [V] with a compound selected from the group consisting of water, an alkanol, ammonia and the like.

The indole derivative of the formula [III], which is used as a starting material in the (a) method mentioned above, can be prepared, for example, by reacting an azide derivative of the formula,

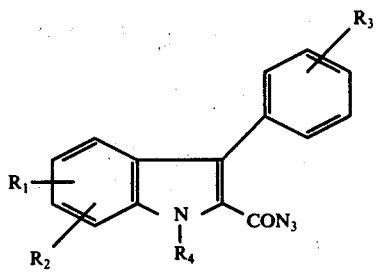

wherein $R_1$, $R_2 R_3$ and $R_4$ are as defined above, with an alcohol such as methanol, ethanol, propyl alcohol and benzyl alcohol or an alkanoic acid such as acetic acid, and formic acid and the like.

The thus obtained indole derivative of the formula [III] can be converted to an acylurea derivative of the formula [IV] by the reaction with an oxidizing agent. As the oxidizing agent, such compounds as ozone, hydrogen peroxide, a peracid (e.g. performic acid, peracetic acid, perbenzoic acid, etc.), chromic acid, a permanganate and the like are preferably used. The reaction can generally be carried out in a solvent at room temperature with ease, but, if necessary, it may be carried out by cooling or heating. As the solvent, which may be varied with the kind of an oxidizing agent to be used, water, chloroform, carbon tetrachloride, acetic acid, formic acid, acetone, alcohols, and the like may be used.

The imidazolidine derivative of the formula [V], which is used as a starting material in the (b) method mentioned above, can be prepared by oxidizing an indoledicarboximide derivative of the formula,

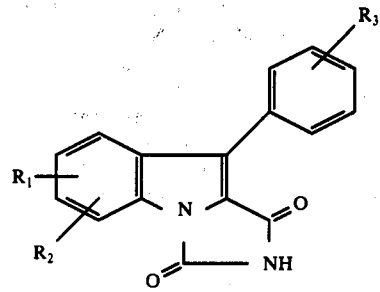

wherein $R_1$, $R_2$ and $R_3$ are as defined above, using an oxidizing agent such as ozone, chromic acid, a permanganate, a peracid (e.g. performic acid, peracetic acid, perbenzoic acid, etc.) and the like.

When an imidazolidine derivative of the formula [V], wherein A together with B forms a

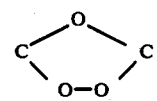

group, which can be obtained mainly by the oxidation with ozone, is reacted with an alkanol, an allophanic acid ester derivative of the formula [IV] wherein $R_5$ is a lower alkoxy group, can be obtained. An allophanamide derivative of the formula [IV] having an amino group as $R_5$ can be obtained by the reaction of an imidazolidine derivative of the formula [V] with ammonia. As the alkanol, methanol, ethanol, propyl alcohol, isopropyl alcohol, and the like are preferable.

On the other hand when an imidazolidine derivative of the formula [V], where A and B are independently a C = O group, which can be obtained by using an oxidizing agent other than ozone or by using ozone under particular conditions, is reacted with an alkanol, water or ammonia, an oxaluric acid ester derivative having an alkoxycarbonyl group as $R_5$, an oxaluric acid derivative having a carboxyl group as $R_5$ or an oxaluramide derivative having a carbamoyl group as $R_5$, of the formula [IV], respectively, can be obtained.

The thhus obtained acylurea derivative of the formula [IV] can be converted to a quinazolinone derivative of the formula [I] with ease by heating or hydrolysis. In the case of the conversion by heating, the acylurea derivative is generally heated to a temperature of the melting point (decomposition) thereof in the absence of a solvent. The reaction mentioned above may also be carried out with ease in the presence of a solvent such as dimethylformamide, dimethylsulfoxide, diglyme or the like having a higher boiling point.

In the case of the conversion by hydrolysis, such a caustic alkali as caustic soda, caustic potash or the like, or such a mineral acid as hydrochloric acid, sulfuric acid or the like are preferably used.

The quinazolinone derivatives of the formula [I] obtained by the process of this invention are useful as excellent anti-inflammatory and analgesic agents with loww toxicity and they are also useful as intermediates for preparing other excellent anti-inflammatory agents and central nervous system depressants.

According to the process of the present invention, the following quinazolinone derivatives, for example, can be obtained.

4-Phenyl-2-(1H)-quinazolinone
4-Phenyl-6-chloro-2(1H)-quinazolinone
4-Phenyl-6-bromo-2(1H)-quinazolinone
4-Phenyl-6-fluoro-2(1H)-quinazolinone
4-Phenyl-6-methyl-2(1H)-quinazolinone
4-Phenyl-6-methoxy-2(1H)-quinazolinone
4-Phenyl-6-nitro-2(1H)-quinazolinone
4-Phenyl-6-trifluoromethyl-2(1H)-quinazolinone
4-Phenyl-6,8-dichloro-2(1H)-quinazolinone
4-Phenyl-6,7-dimethoxy-2(1H)-quinazolinone
4-(o-Chlorophenyl)-6-chloro-2(1H)-quinazolinone
4-(o-Chlorophenyl)-6-nitro-2(1H)-quinazolinone
4-(o-Fluorophenyl)-6-chloro-2(1H)-quinazolinone
1-Methyl-4-phenyl-2(1H)-quinazolinone
1-Methyl-4-phenyl-6-chloro-2(1H)-quinazolinone
1-Methyl-4-phenyl-6-iodo-2(1H)-quinazolinone
1-Methyl-4-phenyl-6-methoxy-2(1H)-quinazolinone
1-Methyl-4-phenyl-6-nitro-2(1H)-quinazolinone
1-Methyl-4-phenyl-6-trifluoromethyl-2(1H)-quinazolinone
1,6-Dimethyl-4-phenyl-2(1H)-quinazolinone
1,8-Dimethyl-4-phenyl-6-chloro-2(1H)-quinazolinone
1-Ethyl-4-phenyl-6-nitro-2(1H)-quinazolinone
1-Ethyl-4-(o-tolyl)-6-chloro-2(1H)-quinazolinone
1-Isopropyl-4-phenyl-6-chloro-2(1H)-quinazolinone
1-Isopropyl-4-phenyl-6-methoxy-2(1H)-quinazolinone
1-Isopropyl-4-phenyl-6-nitro-2(1H)-quinazolinone
1-Isopropyl-4-phenyl-6-trifluoromethyl-2(1H)-quinazolinone
1-Isobutyl-4-phenyl-6-chloro-2(1H)-quinazolinone
1-n-Butyl-4-phenyl-6-chloro-2(1H)-quinazolinone
1-(2,2,2-Trifluoroethyl)-4-phenyl-6-chloro-2(1H)-quinazolinone
1-Cyclopropylmethyl-4-phenyl-6-chloro-2(1H)-quinazolinone
1-Cyclopropylmethyl-4-(o-tolyl)-6-chloro-2(1H)-quinazolinone
1-Cyclopropylmethyl-4-Phenyl-6-nitro-2(1H)-quinazolinone
1-Cyclopropylmethyl-4-phenyl-6-trifluoromethyl-2(1H)-quinazolinone
1-Cyclopropylmethyl-4-phenyl-6-bromo-2(1H)-quinazolinone
1-Cyclopropylmethyl-4-phenyl-6,8-dichloro-2(1H)-quinazolinone
1-Cyclopropylmethyl-4-phenyl-6-methoxy-2(1H)-quinazolinone
1-Cyclopropylmethyl-4-(o-fluorophenyl)-6-chloro-2(1H)-quinazolinone
1-Cyclopropylmethyl-4-(m-chlorophenyl)-6-chloro-2(1H)-quinazolinone
1-Cyclopropylethyl-4-phenyl-6-chloro-2(1H)-quinazolinone
1-Cyclopropylmethyl-4-(o-chlorophenyl)-6-nitro-2(1H)-quinazolinone
1-Cyclohexylmethyl-4-phenyl-6-nitro-2(1H)-quinazolinone The invention is illustrated more particularly by way of the following examples but, as will be more apparent, is not limited to the details thereof.

EXAMPLE 1

To a solution of 2.0 g of ethyl 1-methyl-3-phenyl-5-chloroindole-2-carbamate in 20 ml of acetic acid, a solution of 2.0 g of chromic anhydride in 2 ml of water was added dropwise at 15° – 20° C in 5 minutes. The resulting mixture was stirred at room temperature for 15 hours, and then 50 ml of water was added to the reaction mixture. The resulting reaction mixture was neutralized with concentrated ammonia water and extracted with ether. The extracted ether layer was washed with water, and dried over Glauber's salt. The solvent was removed by distillation under reduced pressure to give 1.92 g of oily ethyl 4-(4-chloro-2-benzoylphenyl)-4-methylallophanate. After dissolving the oily material in 20 ml of ethanol and adding 5 ml of a 20% aqueous solution of caustic soda thereto, the resulting mixture was refluxed for 30 minutes. After removing the solvent by distillation under reduced pressure, the residue was washed with water, collected by filtration and recrystallized from isopropanol to give 1-methyl-4-phenyl-6-chloro-2(1H)-quinazolinone having a melting point of 220° – 221° C.

The starting material was prepared as follows:
A suspension of 5.82 g of 1-methyl-3-phenyl-5-chloroindole-2-carboxylic acid azide in 300 ml of ethanol was refluxed for 2 hours. After cooling the room temperature, the resulting solution was filtered and the solvent was removed by distillation under reduced pressure. The obtained residue was recrystallized from isopropanol to give 5.30 g of ethyl 1-methyl-3-phenyl-5-chloroindole-2-carbamate having a melting point of 123° – 4° C.

EXAMPLE 2

To a suspension of 1.0 g of benzyl 1-methyl-3-phenyl-5-chloroindole-2-carbamate in 10 ml of acetic acid, a solution of 1.0 g of chromic anhydride in 1 ml of water was added dropwise with stirring below 25° C. The resulting mixture was stirred at room temperature for 6 hours, and then 25 ml of water was added to the reaction mixture. The resulting reaction mixture was neutralized with concentrated ammonia water and extracted with ether. The extracted ether layer was washed with water and dried over Glauber's salt. The solvent was removed by distillation under reduced pressure to give 0.94 g of oily benzyl 4-(4-chloro-2-benzoylphenyl)-4-methylallophanate. After dissolving the oily material in 9 ml of ethanol and adding 3 ml of concentrated hydrochloric acid thereto, the resulting mixture was refluxed for 1 hour. After removing the solvent by distillation under reduced pressure, the obtained residue was neutralized with concentrated ammonia water. The obtained crystals were collected by filtration, washed with water and recrystallized from ethanol to give 1-methyl-4-phenyl-6-chloro-2(1H)-quinazolinone having a melting point of 220° – 221° C.

The starting material was prepared as follows:
To a mixture of 30 ml of benzyl alcohol and 130 ml of toluene under reflux, 15 g of 1-methyl-3-phenyl-5-chloroindole-2-carboxylic acid azide was added gradually. After continuing the reflux for 30 minutes, the reaction mixture was cooled. After removing insoluble material by filtration, the resulting solution was condensed under reduced pressure to remove the toluene off, and then the benzyl alcohol was removed by distillation under reduced pressure. The residue was purified by chromatography using 700 g of silica gel and chloroform as a solvent to give 8 g of benzyl 1-methyl-3-phenyl-5-chloroindole-2-carbamate. Recrystallized from ethanol, the obtained crystals have a melting point of 163.5° – 164.5° C.

EXAMPLE 3

To a suspension of 1.0 g of ethyl 3-(o-fluorophenyl)-5-chloroindole-2-carbamate in 10 ml of acetic acid, a solution of 1.0 g of chromic anhydride in 1 ml of water was added dropwise at 15° – 20° C with stirring. After stirring for 15 hours at room temperature, the reaction mixture was neutralized with concentrated ammonia water and extracted with chloroform. The extracted chloroform layer was washed with water and dried over Glauber's salt and the solvent was removed by distillation to obtain 0.8 g of oily material. The oily material was treated with active carbon in ethanol and recrystallized from ethanol to give ethyl 4-(2-(o-fluorobenzoyl)-4-chlorophenyl) allophanate having a melting point of 207° – 207.5° C.

The starting material was prepared as follows:

A solution of 3.0 g of 3-(o-fluorophenyl)-5-chloroindole-2-carboxylic acid azide in 200 ml of ethanol was refluxed for 2 hours. After cooling to room temperature, the reaction mixture was filtered and the solvent was removed by distillation under reduced pressure. The obtained residue was recrystallized from ethanol to give the crystals having a melting point of 130.5° – 132° C.

EXAMPLE 4

3-(o-Fluorophenyl)-5-chloroindole-1,2-dicarboximide ozonide (0.1 g, was added to 2 ml of ethanol and the resulting mixture was refluxed for 1 hour. After cooling, the deposited crystals were collected by filtration to give 0.09 g of ethyl 4-(2-(o-fluorobenzoyl)-4-chlorophenyl)allophanate having a melting point of 208° – 209° C.

The starting material was prepared as follows:

To a suspension of 1.0 g of 3-(o-fluorophenyl)-5-chloroindole-1,2-dicarboximide in 25 ml of acetic acid, a mixture of ozone and oxygen was introduced with stirring. After 30 minutes, the reaction mixture become a solution, and then crystals began to deposit. After introducing a mixture of ozone and oxygen for additional 3 hours, the deposited crystals were collected by filtration and dried to obtain 3-(o-fluorophenyl)-5-chloroindole-1,2-dicarboximide ozonide having a melting point of 136.5° – 7° C. (decomposition).

EXAMPLE 5

Ethyl 4(2-(o-fluorobenzoyl)-4-chlorophenyl)allophanate (0.2 g) was dissolved in a mixture of 6 ml of ethanol and 0.8 ml of a 20% aqueous solution of caustic soda, and the resulting mixture was refluxed for 1 hour. After the ethanol was removed by distillation under reduced pressure, the obtained residue was acidified with concentrated hydrochloric acid and cooled overnight. Then the crystals were collected by filtration and dried to give 0.14 g of 4-(o-fluorophenyl)-6-chloro-2(1H)-quinazolinone having a melting point of over 300° C.

EXAMPLE 6

Ethyl 4-(2-(o-fluorobenzoyl)-4-chlorophenyl)-allophanate (50 mg) was dissolved in dimethylformamide and the mixture was heated to the reflux temperature to deposit crystals. The crystals were collected by filtration and dried to give 4-(o-fluorophenyl)-6-chloro-2(1H)-quinazolinone having a melting point of over 300° C.

EXAMPLE 7

1-(2-(o-Fluorobenzoyl)-4-chlorophenyl)-parabanic acid (0.50 g) was added to 7 ml of water and the mixture was heated at 95° C on a water bath for 3.5 hours. After cooling, the crystals were collected by filtration, washed with ether and dried to give 0.45 g of 5-(2-(o-fluorobenzoyl)-4-chlorophenyl)oxaluric acid having a melting point of 199.5° – 200° C (decomposition).

The resulting compound was subjected to hydrolysis using a similar procedure described in Example 5 to obtain 4-(o-fluorophenyl)-6-chloro-2(1H)-quinazolinone having a melting point of over 300° C.

The starting material was prepared as follows:

To a suspension of 2.0 g of 3-(o-fluorophenyl)-5-chloroindole-1,2-dicarboximide in 30 ml of acetic acid, a solution of 3.0 g of chromic anhydride in 3 ml of water was added and the resulting mixture was stirred at 65° C for 5 hours. After removing the acetic acid by distillation under reduced pressure, 100 ml of water was added to the residue and the solution was extracted with ether. The extracted ether layer was washed with water, dried over Glauber's salt and distilled under reduced pressure to remove the solvent. The residue was washed with n-pentane to obtain 1.74 g of 1-(2-(o-fluorobenzoyl)-4-chlorophenyl)parabanic acid, as an amorphous solid.

EXAMPLE 8

A solution of 0.20 g of 1-(2-(o-fluorobenzoyl)-4-chlorophenyl) parabanic acid in 3 ml of ethanol was refluxed for 5 hours. After cooling, the deposited crystals were collected by filtration to give 0.04 g of ethyl 5-(2-(o-fluorobenzoyl)-4-chlorophenyl)oxalurate having a melting point of 199° – 200° C (decomposition). The filtrate was further refluxed to obtain 0.09 g of additional crystals. The total yield was 0.13 g.

The resulting compound was subjected to hydrolysis using a similar procedure described in Example 5 to obtain 4-(o-fluorophenyl)-6-chloro-2(1H)-quinazolinone having a melting point of over 300° C.

EXAMPLE 9

1-(2-(o-Fluorobenzoyl)-4-chlorophenyl) parabanic acid (0.20 g) was added to 2 ml of concentrated ammonia water and the resulting mixture was stirred at room temperature for 3 hours. The crystals were collected by filtration, washed with water and dried to obtain 0.19 g of 5-(2-(o-fluorobenzoyl)-4-chlorophenyl)oxaluramide. Recrystallized from a mixture of ethanol and dimethylformamide, the crystals showed a melting point of 212° – 212.5° C (decomposition).

The resulting compound was subjected to hydrolysis using a similar procedure described in Example 5 to obtain 4-(o-fluorophenyl)-6-chloro-2(1H)-quinazoline.

EXAMPLE 10

3-Phenyl-5-nitroindole-1,2-dicarboximide ozonide (0.5 g) was added to 25 ml of ethanol and the resulting mixture was refluxed for 30 minutes. After cooling, the deposited crystals were collected by filtration to give 0.41 g of ethyl 4-(2-benzoyl-4-chlorophenyl)allophenate having a melting point of 202° – 203° C.

The resulting compound was subjected to hydrolysis using a similar procedure described in Example 5 to obtain 4-phenyl-6-nitro-2(1H)-quinazolinone having a melting point of over 300° C.

The starting material was prepared as follows:

To a suspension of 1.0 g of 3-phenyl-5-nitroindole-1,2-dicarboximide in 25 ml of acetic acid, a mixture of ozone and oxygen was introduced with stirring. After 2.5 hours, the reaction mixture became a solution. After introducing a mixture of ozone and oxygen for an additional 1 hour, the resulting solution was diluted with water and the formed crystals were collected by filtration and dried to obtain 3-phenyl-5-nitroindole-1,2-dicarboximide ozonide having a melting point of 100° C (decomposition).

What is claimed is:

1. A process for preparing a quinazolinone of the formula,

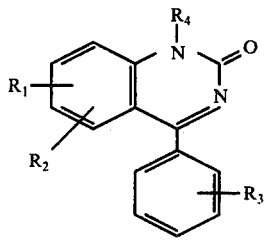 (I)

wherein $R_1$, $R_2$ and $R_3$ are independently a hydrogen atom, a halogen atom, trifluoromethyl, nitro, lower alkyl, or lower alkoxy; and $R_4$ is a hydrogen atom, lower alkyl, polyhalo $C_1$-$C_3$ alkyl or ($C_3$-$C_6$ cycloalkyl) $C_1$-$C_4$ alkyl, which comprises the steps of a. reacting an indole derivative of the formula,

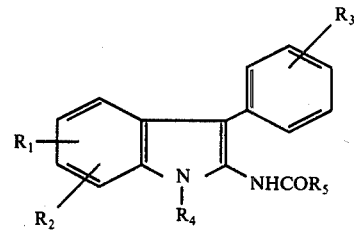 (III)

wherein $R_1$, $R_2$, $R_3$, and $R_4$ are as defined above; and $R_5$ is a lower alkoxy or benzyloxy, with chromic acid or chromic anhydride to form an acylurea of the formula

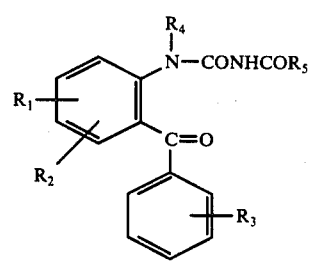 (IV)

$R_1$, $R_2$, $R_3$, $R_4$ and $R_5$ are as defined above; and b. hydrolyzing or heating said acylurea of the formula (IV) to prepare said quinazolinone of the formula (I).

2. A process according to claim 1, wherein $R_5$ is lower alkoxy.

3. A process according to claim 1, wherein $R_5$ is benzyloxy.

4. a process according to claim 1, wherein tthe oxidation reaction is carried out in a solvent selected from the group consisting of water, chloroform, carbon tetrachloride, acetic acid, formic acid, acetone and an alcohol.

* * * * *